(12) United States Patent
Hill (10) Patent No.: US 7,631,567 B1
(45) Date of Patent: Dec. 15, 2009

(54) SYSTEMS AND METHODS FOR COLLECTING PARTICLES FROM A LARGE VOLUME OF GAS INTO A SMALL VOLUME OF LIQUID

(75) Inventor: Steven C. Hill, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 435 days.

(21) Appl. No.: 11/507,203

(22) Filed: Aug. 18, 2006

(51) Int. Cl.
*G01N 1/00* (2006.01)

(52) U.S. Cl. .................................... 73/863.22

(58) Field of Classification Search ........................ None
See application file for complete search history.

(56) References Cited

U.S. PATENT DOCUMENTS

| | | | | |
|---|---|---|---|---|
| 3,518,815 | A | * | 7/1970 | Peterson et. al. ......... 73/863.22 |
| 4,356,009 | A | * | 10/1982 | Calvert ..................... 95/222 |
| 6,087,183 | A | | 7/2000 | Zaromb ................... 436/178 |
| 6,267,016 | B1 | | 7/2001 | Call et al. ............... 73/863.22 |
| 6,337,213 | B1 | | 1/2002 | Simon et al. ............. 436/178 |
| 6,520,034 | B1 | | 2/2003 | Masquelier et al. ...... 73/863.21 |
| 6,565,811 | B1 | | 5/2003 | Zarmob .................... 422/88 |
| 6,642,057 | B1 | | 11/2003 | Zaromb .................... 436/168 |
| 6,682,934 | B2 | | 1/2004 | Jolly et al. ............... 436/73 |
| 6,887,710 | B2 | | 5/2005 | Call et al. ................. 436/53 |
| 6,900,432 | B1 | | 5/2005 | Foulger et al. ............ 250/287 |
| 6,951,147 | B2 | | 10/2005 | Call et al. ............... 73/863.22 |
| 6,955,075 | B2 | | 10/2005 | Carlson et al. ........... 73/28.02 |
| 7,029,921 | B2 | * | 4/2006 | Lee et al. ................. 436/148 |
| 7,062,982 | B2 | | 6/2006 | Coyle et al. ............. 73/863.23 |
| 7,261,008 | B2 | * | 8/2007 | Saaski et al. ............ 73/863.22 |
| 2004/0023411 | A1 | | 2/2004 | Fenn ....................... 436/174 |
| 2004/0025604 | A1 | * | 2/2004 | Call et al. ................ 73/863.22 |
| 2004/0069047 | A1 | | 4/2004 | Coyle et al. ............. 73/28.04 |
| 2004/0089156 | A1 | | 5/2004 | Gartstein et al. ........... 96/53 |
| 2005/0028577 | A1 | | 2/2005 | Chang et al. .............. 73/23.2 |

OTHER PUBLICATIONS

Hinds, William C., Aerosol Technology, Properties, Behavior, and Measurement of Airborne Particles (Wiley, New York, 1999) 2$^{nd}$ edition.

(Continued)

*Primary Examiner*—Robert R Raevis
(74) *Attorney, Agent, or Firm*—Edward L. Stolarun; A. David Spevack (57) ABSTRACT

Systems and methods for collecting particles are provided. A representative system includes an aerosol-into-liquid collector that stores a collection liquid. The aerosol-into-liquid collector also includes a container, a gas inlet, a gas outlet and a source of vacuum pressure such that, when the source of vacuum pressure provides vacuum pressure at the gas outlet, gas with particles entrained therein is drawn into the container through the gas inlet. A well holds a volume of the collection liquid such that at least some of the particles entrained in the gas collide with the collection liquid and adhere thereto. Gas drawn into the container impinges upon an exposed surface of the collection liquid in the well. Forces exerted by the gas do not tend to push the collection liquid out of the well or cause the collection liquid to break into multiple droplets.

10 Claims, 6 Drawing Sheets

OTHER PUBLICATIONS

Belostoki, et al., Combined micro-droplet and thin-film-assisted pre-concentration of lead traces for on-line monitoring using anodic stripping voltammetry, Analytical Bioanalytical Chemistry, 375, 482-488 (2003).

Gridin, et al. "A Renewable Liquid Droplet Method for On-Line Pollution Analysis by Multi-Photon Ionization," Analytical Chemistry, 69, 2098-2102 (1997).

Grinshpun et al., J. Aerosol Sci., 36, 575-591 (2005).

Pan et al., *Aerosol. Sci. Technol.* 38(6), 598 (2004).

Frain, et al., *Aerosol Sci.Technol.* 40(3), 218 (2006).

Virenda Sethi and Walter John, "Particle Impaction Patterns From a Circular Jet", Aerosol Sciences and Technology 18, pp. 1-10, 1993.

\* cited by examiner

SYSTEMS AND METHODS FOR COLLECTING PARTICLES FROM A LARGE VOLUME OF GAS INTO A SMALL VOLUME OF LIQUID

GOVERNMENT INTEREST

The invention described herein may be manufactured, used, and licensed by or for the United States Government.

BACKGROUND OF THE INVENTION

1. Field of the Invention

This invention pertains generally to measurement of analyte in gas-borne particles, and particularly to collection of gas-borne particles into a liquid so that analytes in the particles can be analyzed.

2. Description of the Related Art

Devices are needed that can quickly detect and identify the presence of materials, such as harmful materials, in airborne particles. Airborne infectious agents such as bacteria and viruses can transmit diseases of humans, other animals, and plants. Some of these infectious agents, as well as some protein toxins, have been used as biological-warfare (BW) agents. Some airborne proteins and pollens cause allergies. Here, "airborne particles" or "gas-borne particles" refer to both the solid particles and liquid droplets in an air or gas sample.

A group of particles in an air sample, of either indoor or outdoor air, may include many types of organic and inorganic materials and many types of bacterial and other biological materials. Individual particles may be homogenous or may be a complex mixture of materials. Identification of specific bacteria, viruses, or proteins, and many other types of complex chemicals that may be mixed in atmospheric particles requires the collection of those particles so that they can be analyzed by appropriate techniques, e.g., immunoassay for bacteria, protein allergens, and other biological materials; culturing for bacteria and viruses; mass spectrometry for organic chemicals. For identification of specific bacteria or proteins using biochemical methods, the collection of these particles into a liquid is needed. For many types of analyses, e.g., single-particle infrared or Raman analysis, collection of airborne particles onto filters or other solid surfaces is desired.

An overview of aerosols and some of the principles relevant for collection of aerosols are provided by William C. Hinds, Aerosol Technology, Properties, Behavior, and Measurement of Airborne Particles (Wiley, New York, 1999) $2^{nd}$ edition, which is herein incorporated by reference. Throughout this application we will refer to this as "Hinds" and may give specific pages, equation numbers, etc.

Investigators have worked for years to develop instruments for collecting aerosol particles into liquids. The literature describing different methods is large. Methods for collection of airborne particles, including methods for collection of particles into liquids, have been reviewed by M. L. Muilenberg, "Sampling Devices," Immunology and Allergy Clinics of North America, 23, 337-355 (2003). Liquid-impingement methods are widely used, but the volumes of liquid needed for microfluidic analyses are typically far smaller than are used with liquid impingers.

Some methods of collecting particles into a liquid are briefly summarized in the paper by I. Belostotski, V. V. Gridin, I. Schecter, and C. N. Yarnitzky, "Combined micro-droplet and thin-film-assisted pre-concentration of lead traces for on-line monitoring using anodic stripping voltammetry," Analytical Bioanalytical Chemistry, 375, 482-488 (2003), especially in the introduction of that paper.

S. Zaromb, "High-Throughput Liquid-Absorption Air-Sampling Apparatus and Methods," U.S. Pat. No. 6,087,183, describes an apparatus to collect particles from air into liquid. In his apparatus, 200 to 300 liters/min of air are drawing asymmetrically into a cylinder. This rapid flow of air swirling in the cylinder causes the liquid at the bottom of the cylinder to rise and also swirl inside the cylinder. Then particles from the air are collected into the liquid. The apparatus uses at least a few milliliters of liquid per sample, and evaporation may be expected to be significant.

P. T. Call, V. M. Kenning, C. Call, J. G. Birmingham, and D. J. Hammerstrom, "Impact Particulate Collector Using a Rotary Impeller for Collecting Particulates and Moving a Fluid," U.S. Pat. No. 6,267,016 B1 (2001), describe another means to collect particles into a liquid. The airborne particles impact upon a rotating surface. A liquid is injected into the cavity that contains this rotating surface, and the particles may be washed into this liquid or may impact directly into the liquid.

P. J. Coyle, T. A. Pletcher, T. J. Davis, and S. Mangru, "Method and Apparatus for Concentrated Airborne Particle Collection," U.S. Patent Application Publication, 2004/006907 A1, which is herein incorporated by reference, describe an apparatus to collect particles from a large volume of air into a relatively small volume of liquid in which a hydrophobic membrane establishes a "controllable air-fluid boundary" between a separation section where the particles are in air, and a capture section in which the particles are transported in liquid. A corona charger may be used to charge the aerosol so that the particles may be focused into the liquid stream.

Agranovski, V. Agranovski, S. A. Grinsphun, T. Reponen, and K. Willeke, "Collection of Airborne Microorganisms into Liquid by Bubbling through Porous Medium," Aerosol Science and Technology, 36, 502-509 (2002), describe a means to collect aerosols by bubbling them through a fibrous filter that is immersed in water. They demonstrate very efficient collection for an air sample of up to 4 liters/minute running for up to 8 hours.

D. A. Masquelier, F. P. Milanovich and K. Willeke, "High Air Volume to Low Liquid Volume Aerosol Collector," U.S. Pat. No. 6,520,034 B1, which is herein incorporated by reference, provide an apparatus to efficiently collect particles from a high volume (e.g., 225 Lpm) of air into a "collecting liquid having a volume not greater than about 100 to 300 microliters." They provide a means to reduce the loss of the collection liquid, which they need to reduce because they impinge 225 liters/min of air onto this liquid in order for the particles in the air to be transferred to the liquid. This impinging of air into the liquid causes some of the liquid to form airborne droplets and some of the liquid to evaporate. They collect for re-use the liquid droplets, but not the evaporated liquid. The device is, small (typically 2 liters), lightweight (typically less than 1 Kg), and has low power requirements.

V. V. Gridin, I. Litani-Barzilai, M. Kadosh, and I. Schecter, "A Renewable Liquid Droplet Method for On-Line Pollution Analysis by Multi-Photon Ionization," Analytical Chemistry, 69, 2098-2102 (1997), which is herein incorporated by reference, describe collection of gasses and aerosol particles into a pendant water droplet, where they are analyzed. The collection efficiency is not expected to be large, but would be sufficient for cases where particles that are in high concentration, and/or when the collection times are long.

V. Gartstein and A. D. Willey, "Dynamic Electrostatic Aerosol Collection Apparatus for Collection and Sampling Airborne Particulate Matter," U.S. Patent Application Publication, 2004/0089156 A1, published May 13, 2004, describe a method of collection of aerosol particles by passing them through a spray of charged droplets that act as electrostatic collectors. The particles may be given a charge opposite to that of the droplets to enhance the collection efficiency. The liquid is re-circulated and is chosen to have a low volatility to reduce evaporative losses. See also J. B. Fenn's, "Electrospray Air Sampler," U.S. Patent Application Publication 2004/0023411 A1, published Feb. 5, 2004.

SUMMARY OF THE INVENTION

Systems and methods for collecting particles are provided. In this regard, an embodiment of such a system comprises an aerosol-into-liquid collector. The aerosol-into-liquid collector is operative to position a collection liquid to capture particles entrained in a gas. The aerosol-into-liquid collector comprises a nozzle and a well. The nozzle is operative to direct the gas with the particles entrained therein at a velocity of at least 10 meters per second. The well is operative to hold a volume of the collection liquid and is positioned such that at least some of the particles entrained in the gas collide with an exposed surface of the volume of the collection liquid and adhere to the volume of the collection liquid. The gas, with the velocity of at least 10 meters per second, departs the nozzle and impinges upon the exposed surface of the volume of the collection liquid and does not push the volume of the collection liquid out of the well and does not cause the volume of the collection liquid to break into multiple droplets.

Another embodiment of a system for collecting particles comprises an aerosol-into-liquid collector that is positioned to capture particles entrained in a gas. The aerosol-into-liquid collector comprises an aerosol-particle-handling subsystem, a reservoir of collection liquid and a well. The aerosol-particle-handling subsystem incorporates a gas-tight container, a gas inlet, a gas outlet and a source of vacuum pressure, the source of vacuum pressure being operative to draw gas, with particles entrained therein, into the gas-tight container. The well communicates with the reservoir and is operative to hold a volume of the collection liquid. The well is positioned within the gas-tight container such that the gas drawn into the gas-tight container through the gas inlet is directed toward the well such that at least some of the particles entrained in the gas collide with an exposed surface of the volume of the collection liquid and adhere to the collection liquid located in the well. Forces exerted by the gas impinging upon the exposed surface of the volume of the collection liquid are relatively symmetric about an average normal to the exposed surface such that the gas does not tend to push the volume of the collection liquid out of the well. At least a portion of the well is hydrophobic with respect to the collection liquid such that the volume of the collection liquid tends to stay in the well.

An embodiment of a method for collecting particles comprises: positioning a volume of a collection liquid within a well such that a surface of the collection liquid is exposed; using surface tension of the exposed surface of the volume of the collection liquid and the interfacial tension between the collection liquid and the well to retain the collection liquid within the well, with an effect of the surface tension of the exposed surface of the volume of the collection liquid and the interfacial tension between the collection liquid and the well exceeding an effect of gravity in maintaining the collection liquid within the well; and directing a jet of gas, which contains particles, toward the volume of the collection liquid in the well such that the gas impinges upon the exposed surface; wherein a velocity of the jet of gas impinging upon the exposed surface of the volume of the collection liquid permits particles of less than 2 micrometers in diameter to be collected into the collection liquid while the surface tension of the exposed surface of the volume of the collection liquid and the interfacial tension between the collection liquid and the well prevent the collection liquid in the well from breaking into multiple droplets and from being pushed from the well Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Systems and methods for collecting particles into liquid and analyzing the particles are provided. In this regard, some embodiments potentially provide one or more of the following characteristics. That is, some embodiments: (i) are sensitive to small numbers of particles in the air; (ii) are specific for the specific biomaterials the user desires to detect; (iii) provide a rapid response, with no more than a short delay (e.g., 3 minutes) between the time the analyte aerosol enters the instrument and the time the instrument indicates that an analyte has been identified; (iv) can run continuously; (v) has a low requirement for consumables; and (vi) has little need for operator time. If an aerosol into liquid collector, as part of an instrument to detect harmful aerosols, can collect the particles from a large volume of gas such as air into a small volume of liquid, then the overall instrument can be more sensitive and have a more rapid response. It is easier to detect a small number (e.g., 20) suspect particles in a small, e.g., 100 nL, volume of liquid than it is to detect this number in a larger, e.g., 0.1 mL of liquid. The cost of consumables such as antibodies, or nucleic acid probes and enzymes, can be so high that instruments that could run continuously and give a rapid response (e.g., in 10 minutes) are too expensive to run continuously.

If an instrument that collects and analyzes airborne particles does not lose a large amount of the collection liquid during the collection of the particles, it can have a lower requirement for consumables. For applications this lower requirement for all liquids and consumable items is very important. For some other applications, the collection liquid is as inexpensive as pure water, and the instrument is used where water is readily available. Even for these applications the ability of the ALC to collect airborne particles into a small volume of collection liquid can still be highly valuable because the particles are collected into such a small volume of liquid that relatively little reagent must be added to the small volume of collection liquid in order to analyze the collected sample.

There is a need for improved aerosol-into-liquid collectors that collect the particles from a large volume of gas such as air into a small volume of liquid and that provides this small volume of liquid as an input to an instrument that can identify analytes in the particles or otherwise characterize the particles. The importance of this need is augmented by the progress being made in developing methods for sensitively measuring the amounts of analytes in very small sample volumes. For example, developments in microfluidic techniques and "lab-on-chip" techniques provide hope for the development of a continuously running aerosol identifier that may: (a) be highly specific, (b) consume so little reagent for each analysis that it may be run essentially continuously, and (c) lend itself to an automated analysis.

Figure 1:
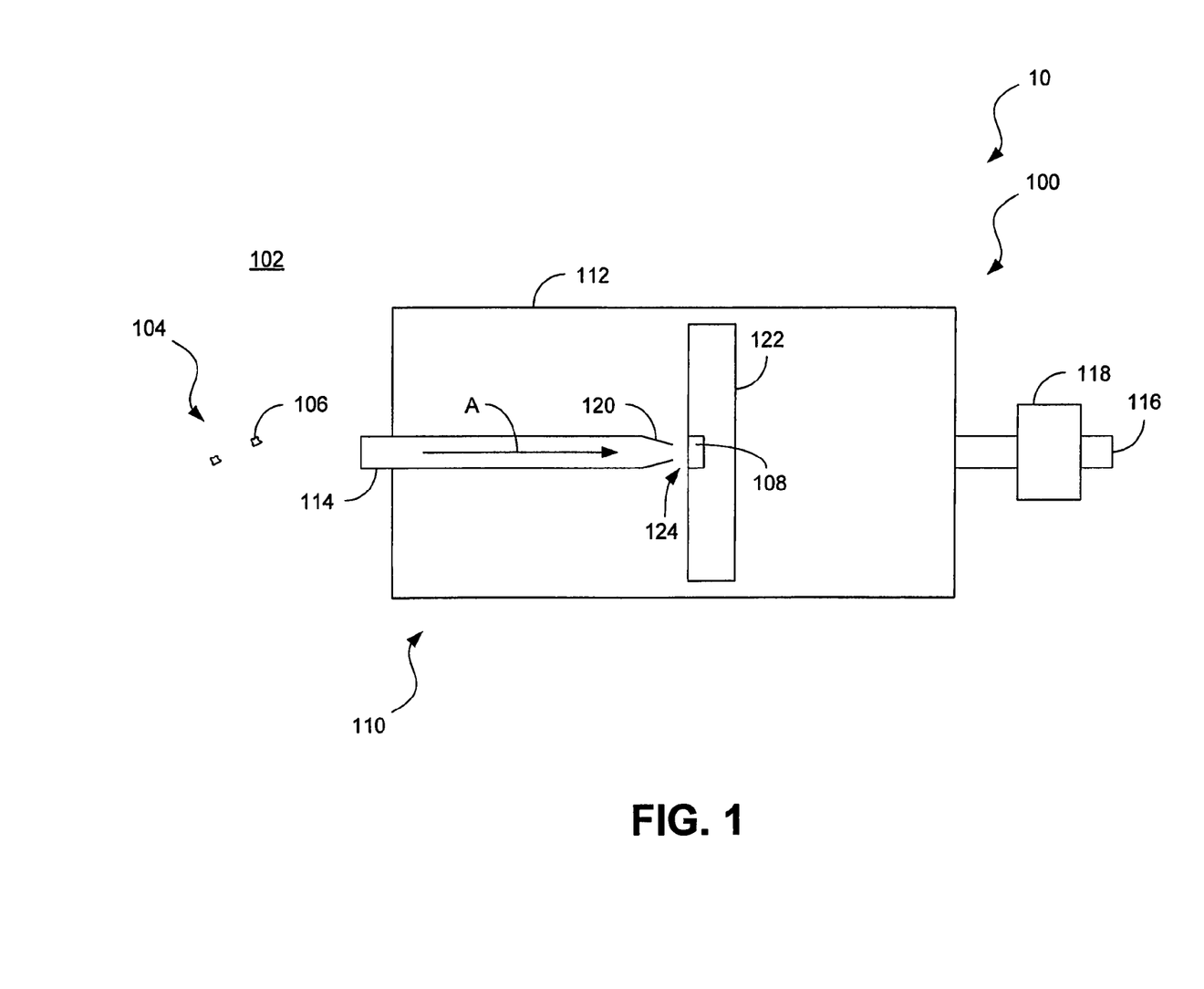
FIG. 1 is a schematic illustration of a side view of an embodiment of a system for collecting particles.

Referring now to the drawings, FIG. 1 is a schematic diagram illustrating an embodiment of a system for collecting particles. In particular, system 10 incorporates an aerosol-into-liquid collector (ALC) 100. The ALC 100 is immersed in a gas 102, such as the atmosphere, having particles 104 therein. Generally, the particles are of many types. For instance, the particles may be liquid, solid, or a mixture of liquid and solid. Some of these particles may be particles of interest (POI) 106. The purpose of the ALC 100 is to collect particles from gas 102 into a collection liquid (CL) 108.

The particles to be collected into the CL have sizes within a preselected range of sizes. In some embodiments, the smaller size of the preselected range of particle sizes is about a 1 micrometer diameter. In other embodiments, the smaller size of this preselected range of sizes is about 0.4 micrometer diameter. For many of the envisioned embodiments, the smaller end of the preselected range of sizes is somewhere between 0.1-micrometer diameter and 3-micrometer diameter. "Particle diameter" for nonspheres is approximate, and is similar to "aerodynamic particle size," or average diameter in most cases of atmospheric particles, and particles which are not highly eccentric.

Embodiments may also collect particles that have sizes outside the preselected range of sizes. Because the methods used here for collecting the particles into the CL are based on impaction of particles into the CL, the larger particles can be easier to collect than the smaller particles. Methods and apparatus for removing particles from a volume of air or an air sample are well known, and so we do not discuss the removal of large particles, e.g., particles larger than 10- or 50-micrometer diameter, but will instead focus upon the smaller end of the preselected range of sizes.

The CL used could be water or some other liquid. In the descriptions here we emphasize aqueous solutions because water is inexpensive and biochemical assays are usually done in aqueous solutions. For some other applications, a nonpolar (hydrophobic) CL may be more appropriate, for example, for the collection of atmospheric particles for real-time analyses of nonpolar organic compounds. Some main parameters that may be relevant in choosing a CL for different applications of the ALC are the compatibility of the CL for whatever analysis method will be used, the polarity, the ability to solvate ions or molecules of interest, the viscosity, the vapor pressure in the relevant temperature range, and the cost.

In most of the description below, we assume aqueous solutions having a viscosity similar to pure water or sea water. That is, the CL does not have so much dissolved solute such as sucrose, or so much additional other liquid such as glycerol, that its viscosity is far larger than sea water. We make that assumption because of what we are assuming for the analyzer that this ALC feeds into, and because if the viscosity is too high a variety of processes such as diffusion of antibodies to the surface of a bacterium in the CL can be far smaller, and enzymes and antibodies may not bind as the do in more dilute aqueous solutions. The ability to impact particles into a CL without blowing the CL into dispersed puddles or little droplets is, of course, dependent upon the viscosity of the CL.

As shown in FIG. 1, ALC 100 includes an aerosol-particle-handling subsystem 110. The subsystem 110 incorporates a container 112, such as a gas-tight container (GTC), a gas inlet 114, a gas outlet 116 and a source of vacuum pressure 118. For some embodiments, such as those in which the gas is already at a relatively high pressure, a GTC and source of vacuum pressure 118 may not be needed. Preferably, the gas inlet is a nozzle 120. In some embodiments the gas inlet is a tube pneumatically connected to a nozzle.

The source of vacuum pressure 118, such as a vacuum pump, preferably has a gas-tight connection to the gas outlet 116. In this configuration, when the source of vacuum pressure generates a vacuum, gas is drawn into the container through the nozzle with as high a velocity as is desired. Thus, the source of vacuum pressure functions as a means to create a difference in pressure across the gas inlet.

A collection-liquid container (CLC) 122 also is provided that includes a well 124. The well holds a volume of the collection liquid (VCL). The well is positioned within the path of the gas, which is now a jet of gas (JOG) (depicted by arrow A), so that when the vacuum generated is sufficient to draw the gas into the container 112 with a sufficient velocity, a substantial fraction of the particles within the preselected size range that are carried in the gas are caused to collide with an exposed gas-liquid surface of the VCL. The particles that collide with the VCL may adhere to the VCL and thus may be collected by the VCL in the well.

A novel feature of this embodiment of the ALC 100 is that it exhibits an ability to collect into a tiny volume of CL very small particles without blowing the CL out of the well, or into little droplets, or otherwise dispersing the CL, as will be described in detail below. One reason to attempt to avoid blowing the CL out of the well is that this approach tends to reduce the amount of CL used. In some existing devices that collect particles into liquid, the air impacts onto the liquid is such a way that the liquid is very much disturbed, and droplets of the liquid are dispersed into the air where they tend to evaporate relatively rapidly. These droplets may be caught again and fed back into the larger volume of liquid, but any particles collected into the CL may then be caught at least temporarily on whatever surfaces these droplets came in contact with. Preferably, the CL is maintained in the well in one contiguous body. The CL in the well may extend a little outside the well so that particles in the JOG can deposit into the CL more efficiently, but this extension outside the well is contiguous and controlled.

Typically, the surface area of the gas-liquid interface at maximum extension is not larger than 2 to 3 times the cross sectional area of the well, and in some embodiments is only a little larger than the cross sectional area of the well. Note that the JOG does not blow the CL out of the well, but in some embodiments the CL is pushed a little bit out of the well by applying pressure to the non-exposed part of the CL in the well in order to expose a little more of the CL.

The well 124 that holds the VCL is positioned sufficiently close to the nozzle so the velocity of the JOG near the gas-liquid surface is sufficiently large so that a substantial fraction of the particles within the preselected range of sizes are caused to impact into the VCL at the gas-liquid surface. Additionally, the well is positioned relative to the nozzle such that the JOG impinges upon the gas-liquid surface in such a manner that any forces on the VCL arising from the JOG are relatively symmetric about an average normal to the gas-liquid surface. This is done so that the JOG does not tend to push the VCL out of the well. Note that in FIG. 2, the exposed gas-liquid surface 230 of the volume of LC contained in the well 124 is depicted. Arrow B represents the average normal to the gas-liquid surface.

Figure 2:
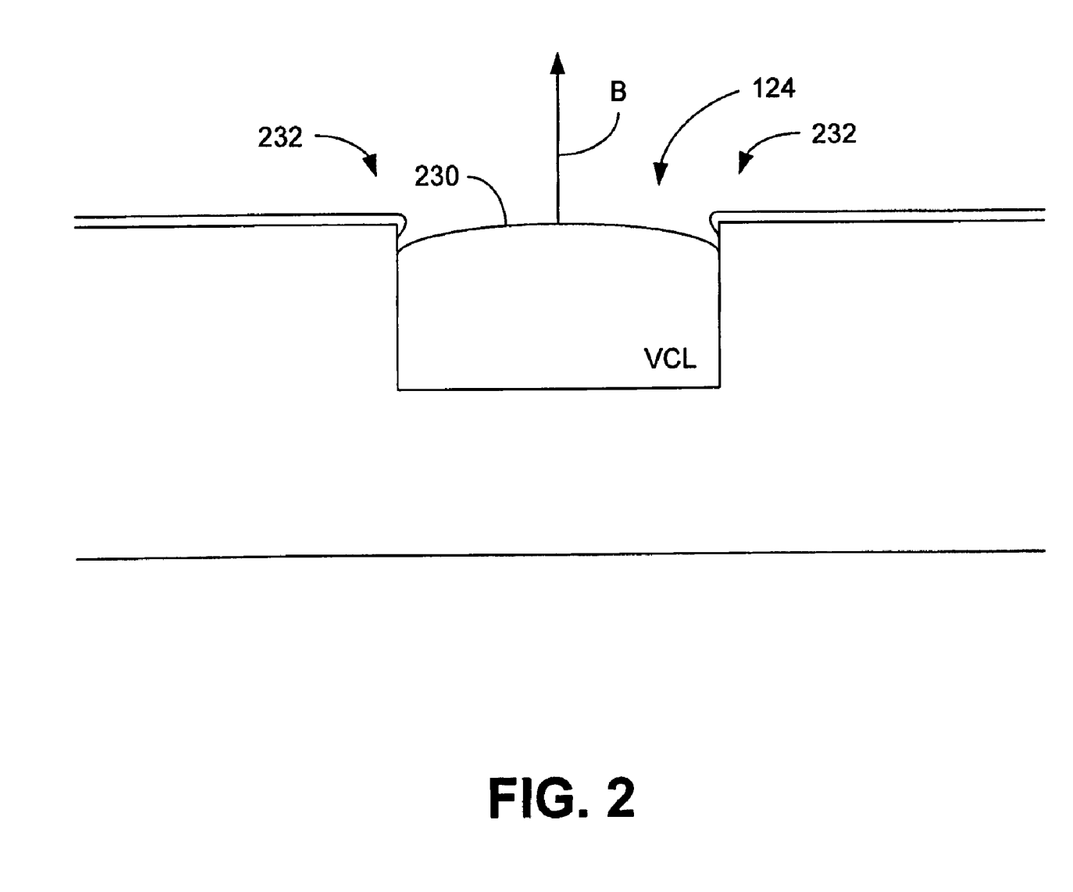
FIG. 2 is a schematic illustration of a side view of an embodiment of a system for collecting particles, showing detail of a well.

With reference to FIGS. 1 and 2, the collection of particles into the CL can be accomplished as follows. The CL is placed in the well 124 such as by, for example, using a syringe or ejecting droplets from a droplet ejector. The VCL in the well is then exposed to the JOG exiting the nozzle 120.

A source of vacuum pressure creates a partial vacuum that draws gas 102, and any particles contained therein, through the gas inlet 114 and into container 112. From there, the gas exits the nozzle as a JOG and then exits the container through the gas outlet 116.

As the JOG passes through the nozzle, the particles carried in this JOG move toward the VCL. The momentum of the particles moving toward the VCL increases the fraction of the particles combining with the VCL.

After the VCL has been exposed to the JOG and to the particles entrained in the JOG, so that those particles 124 may combine with it, it is termed an exposed volume of the collection liquid (EVCL).

To describe quantitatively the collection process and to understand the key design concepts relative to the velocity of the JOG, the nozzle and well diameters, the nozzle-to-CL-surface distance and alignment, and other parameters, it is useful to state some of the key expressions that have been developed to describe the impaction process. Such expressions have been used in numerous articles and books for many years. Here we rely primarily on the summary as presented by Hinds, especially pp. 121-128.

The Stokes number, also known as the impaction parameter, is defined for an impactor as $$Stk = d^2 C_c \rho_p V / 9 \eta D,$$

where the nozzle exit has a circular cross section of diameter D, the gas exits the nozzle with an average velocity of V and has a viscosity of $\eta$, the particle diameter is d and the particle density is $\rho_p$. The Cunningham slip correction factor is $C_c$. The Stokes number is the ratio of the particle stopping distance in a gas moving in velocity V to the radius of the jet exiting the nozzle.

It has been found by computational analysis and experimental work (see, e.g., Hinds, and the references he cites) that for a variety of "well designed" nozzles, greater than 50% of the particles having Stk>0.24 are impacted onto the surface below the nozzle, and less than 50% of the particles having Stk<0.24 are impacted. The cutoff size $d_{50}$ is defined so that more than 50% of the particles having diameters larger than the $d_{50}$ are impacted, and less than 50% of the particles having diameters smaller than the $d_{50}$ are impacted (see Hinds, pp. 125-130). Defining $Stk_{50}$ as the Stokes parameter for 50% collection efficiency, the above expression can be solved for $d_{50}$ as, $$d_{50} C_c^{1/2} = [9 D \eta Stk_{50} / V \rho_p]^{1/2}$$

or in terms of Q, the flow rate of gas through the nozzle, as $$d_{50} C_c^{1/2} = [9 \pi D^3 \eta Stk_{50} / 4 \rho_p Q]^{1/2}.$$

We define the impaction efficiency as the fraction of particles that impact onto the surface, whether or not they remain attached to the surface. We define the collection efficiency as the fraction of particles that impact with the surface and remain attached at the end of the measurement. For most of the following discussion, we will assume that for collection of particles into liquid, essentially all the particles that collide with the liquid remain attached to the body of liquid in many cases penetrating through the surface of the liquid and being completely surrounded by liquid. So we will assume the collection efficiency and impaction efficiencies are the same. That assumption may not always be true, but: (a) we believe that in most cases it is possible to choose a liquid for the particle types of interest so that the collection and impaction efficiencies are similar if not almost identical, and (b) even if the collection efficiency is, for example, only 60% of the impaction efficiency, still the following analysis describes the key features of the present invention. Therefore, we will continue using the term collection efficiency, but with the understanding that for some cases, e.g., a very hydrophobic particle colliding with a hydrophilic liquid such as water, the collection efficiency may be lower.

In the expressions above, all particles that impact onto the plate downstream from the nozzle are included in the collection efficiency. However, we are interested in the particles that are collected into the CL that is in the well or protruding from the well. The deposition pattern of particles on a surface below a nozzle are illustrated in a paper by Virendra Sethi and Walter John, "Particle Impaction Patterns from a Circular Jet," Aerosol Science and Technology, 18, 1-10 (1993), herein incorporated by reference. In particular, Sethi and John's FIG. 4, they show that for $(Stk_{50})^{1/2} > 0.8$ the large majority of the particles are deposited within a circle having a radius of the nozzle exit. For particles having $(Stk_{50})^{1/2} < 0.5$ or so, approximately 50% of the impacted particles are impacted outside this circle, but still close to a circle having the radius of the nozzle edge. Therefore, we can see that for collecting small particles into a small volume of liquid: (a) having $(Stk_{50})^{1/2} = 0.5$ for the lower-size-limit for the particles of interest may be very adequate, and the collection efficiency may be around 30%, (b) having a well that has a diameter 10% or 15% larger than the nozzle may significantly increase the collection efficiency for particles having $(Stk)^{1/2}$ in the range of 0.45 to 0.7, and (c) having $(Stk)^{1/2} > 0.8$ and a well with a diameter about equal to that of the nozzle edge should result in a collection efficiency of greater than 85%. Therefore, we define $d_{w85}$ as the diameter of the particles for which 85% of the particles are collected into a well for the case where the diameter of the well and of the nozzle are the same $$d_{w85} C_c^{1/2} = [9 \pi D^3 \eta Stk_{w85} / 4 \rho_p Q]^{1/2},$$

and where, from the Sethi and John data and from Hinds' description and cited references, $Stk_{w85}$ is about 0.8.

The above expressions for $d_{50}$ and $d_{w85}$ illustrate that to achieve good collection efficiency for the smaller diameter particles we should decrease D/V or $D^3/Q$. Here, to decrease D/V, we decrease D faster than V.

There are three main reasons we emphasize the decrease in D in order to achieve the small $d_{50}$ and $d_{w85}$ desired.

(a) By decreasing D the volume of collection liquid in the well is decreased without needing to decrease the depth of the well further than it already is. The well depth is of course kept small to keep the total volume in the well small, but it does not make sense to achieve a small volume by making an extremely thin layer in a well with large D, at least in part because the evaporation would be a larger problem.

(b) As the diameter of the nozzle exit D decreases, there is a decrease in the spatial and temporal fluctuations in the JOG. Such fluctuations can tend to push the CL out of the well because they result in asymmetric forces on the CL in the well. For a circular pipe of diameter D carrying a gas that has a density $\rho_a$ and a viscosity of $\eta$, the Reynolds number is $$Re = \rho_a V D/\eta,$$

where V is the average velocity of the gas in the pipe. For air at 20° C. and 1 atmosphere pressure, this expression is $$Re = 66VD,$$

for V in m/s and D in mm. Typically, the end of a nozzle is a short circular pipe as illustrated in Hinds, p. 124, FIG. 5.7, or in Sethi and John, FIG. 1. If the D for the exit of the nozzle is 1 mm, and V is 20 m/s, then Re=1320. Typically, the flow in pipes is laminar for V<2000.

We rewrite the above expressions for $d_{50}$ and $d_{w85}$ in terms of Re as, $$d_{50} = D[9\rho_a \text{Stk}_{50}/(ReC_c\rho_p)]^{1/2}.$$

That shows that for a given Re, the cutoff size $d_{50}$ is proportional to D. The above expression suggests that to keep the turbulence low, the Re could be held constant while D is decreased.

The cutoff diameter ($d_{50}$) of a round jet impactor, impacting particles onto a flat surface, is about 1.3 μm if the flow rate is 1 L/min, and the jet diameter exiting the nozzle is 1 mm diameter. See Hinds, Section 5.5, especially the example on p. 127. For the problem we are primarily interested in, where we want to keep the VCL very small, the diameter of the hole should probably be about 1 mm or less. A flow rate through the nozzle of 1 L/min is typical for the air-to-air virtual impactor concentrators we have used (e.g., as purchased from DYCOR), and is a rate that is very reasonable to design for. At a flow rate of 1 L/min, the velocity of the JOG exiting the 1 mm-diameter exit of the nozzle is 21 m/s.

An improved collection efficiency can be obtained if the distance from the nozzle to gas-liquid surface of the liquid in the well is less than the nozzle diameter, as shown by Grinshpun et al., J. Aerosol Sci., 36, 575-591 (2005)), herein included by reference, in studies using commercially available particle collectors which impact particles onto a solid flat surface (e.g., adhesive covered plastic). In the case of the Impactor I-1 studied by Grinshpun et al., with a flow rate of 20 L/min and nozzle diameter of 2.15 mm, the flow velocity exiting the nozzle is 45 m/s.

(c) As the diameter of the well decreases, the CL in the well tends to be more stable, first because of the surface tension at the gas-liquid interface, and second, because the material in the well and near the rim of the well and immediately outside the well can be chosen so as to result in a relatively low interfacial tension when the CL is in the well, but result in a higher interfacial tension if the CL moves out of the well. With respect to surface tension alone, it is known that a small (e.g., 0.02-mm-diameter) droplet of water is pulled into a spherical shape by surface tension, which is far more important than gravitational forces in this case, but that a large (e.g., 3-cm-diameter-) mass of water is distorted by gravitational and aerodynamic forces which tend to be stronger than the surface tension forces.

With respect to interfacial forces, the designer of a particular ALC has considerable latitude in choosing combinations of well and CL that achieve sufficient stability. The ability to achieve stability increases as the diameter of the well decreases. As stated above, the main example collection liquids in which we have chosen to illustrate the ALC are aqueous solutions. Assume, for an example, an aqueous solution with dissolved salts with concentrations similar to those in sea water. This solution is strongly hydrophilic. Therefore, the inside of the well, especially that part of the inside of the well that is designed to be in contact with the CL, is chosen to be of a hydrophilic type of material, which has a relatively low interfacial tension at the liquid-well interface. The aqueous solution tends to "wet" the hydrophilic material. In some of our experiments, we have used glass for this material. For the glasses we have used, the meniscus bends downward, because of gravity, when the well faces upward as it does in FIG. 2. The water wets the glass.

Additionally or alternatively, the surface immediately outside the well, or even just inside the rim of the well, can be chosen at least in part because the interfacial tension at an interface between this surface and the CL is relatively high. For example, for many embodiments, when the CL is an aqueous solution this surface immediately outside the region that is in contact with the CL in the well preferably is hydrophobic. If a JOG impinges on this CL with a velocity sufficient to begin to move the CL out of the well, more of the CL will move into contact with a hydrophobic surface, and so the total interfacial surface tension increases, and so the CL tends not to move out of the well. That is, the well is designed so that it takes a relatively large amount of energy to blow the CL out of the well. In a well with a larger diameter, the relative importance of these surface and interfacial tension forces, which can be designed to increase the stability of the CL in the well, is smaller. But in a well with a smaller D, the importance of the surface and interfacial tension forces is greater. That is, the well is designed so that it takes a relatively large amount of energy to blow the CL out of the well.

To provide a little more detail on the above, in some embodiments, such as the embodiment of FIG. 2, the region 232 around the rim of the well is hydrophobic with respect to the CL. In some of these embodiments, this characteristic can be provided by a layer of material and/or other form of surface treatment, for example. In embodiments where the CL is aqueous and the surface of the CLC at least immediately outside the well and the region 232 around the rim of the well are hydrophobic, the well may have a somewhat larger diameter than the nozzle 120. If the VCL added to the well is sufficient so that the CL is in contact with even a little of the hydrophobic surface, then the meniscus of the VCL typically points outward from the well. The velocity profile of the JOG exiting a nozzle is highest near the axis and lowest at the nozzle edge, and is typically parabolic. Because of this higher velocity of the JOG near the axis of the well and the nozzle, when the JOG blows on the VCL in the well, and protruding toward the nozzle, this JOG initially tends to flatten the meniscus, and can even make a dip in the protruding meniscus. In doing so it can decrease the surface area of the CL protruding toward the nozzle, and therefore, decrease the total surface tension forces. The interfacial tension forces will increase. Notably, in this case, the force exerted by the JOG does not strongly tend to push the VCL out of the well, unless the well is so full of CL that any pushing down of the protruding meniscus expands the CL into regions completely out of the well.

Stated differently, in those embodiments in which the surface on the outside of the well and a portion of the wall in the well is made from a material that has a high interfacial tension with the CL, and where the liquid surface extends to near the rim of the well, the meniscus bows outward, toward the nozzle. The velocity profile of the JOG exiting the nozzle is approximately parabolic with the highest velocity on the axis, and so the greatest force of the JOG is near the axis. Therefore, the greatest force pushing the surface of the liquid back into the well is on the part of surface that is most bowed out, the part nearest the axis. As a result, the force exerted by the JOG has less of a tendency to blow the liquid out of the well than if the diameter were larger or if the region near the rim and just outside the well had a lower interfacial tension with the CL.

Note that if the liquid is hydrophobic instead of hydrophilic, then the surfaces that are hydrophobic (for a hydrophilic CL as discussed above) should instead be hydrophilic, and the surfaces that should be made hydrophilic (for a hydrophilic CL) should instead be made hydrophobic.

(d) The damping of perturbations or distortions in the CL in a small-diameter well should be more rapid than they would be for larger diameter wells. Because the well has such a small diameter, the frequency of any resonant wave in on the CL at the liquid-gas interface should be high. Higher frequency acoustic waves tend to be damped more rapidly than lower frequency waves.

So we have described several reasons why decreasing the diameter of the well and the diameter of the nozzle can lead to increased stability of the CL in the well.

We now discuss some aspects of designing the system so that the forces of the JOG on the CL in the well largely cancel each other, in order to reduce the difference in the force of the JOG on the CL from one side of the well to the other, and to a lesser extent from the parts closer to the axis of the well versus the parts farther from the axis.

We note that it is not the total force of the JOG on the CL in the well that causes the CL to be pushed from the well. Rather, it is the difference in the forces (on the gas-liquid surface of the CL) between one region on this surface and another. For example, in an embodiment in which the nozzle and well are circular and where the axis of the nozzle and the axis of the well are aligned, and where the gas exiting the JOG is laminar, the forces from the JOG on the CL in the well are axisymmetric, at least to first order. In this case, the forces exerted by the JOG on the CL in the well tend to cause axisymmetric modifications of the gas-liquid surface. Such axisymmetric modifications can lead to the CL becoming unstable. However, in our experience these axisymmetric modifications can be relatively large without the CL being pushed from the well (when the diameter of the well is small as discussed above). On the other hand, if the axis of the nozzle is tilted relative to the axis of the well by even a few, e.g., 5 degrees, the JOG may cause a non-axisymmetric differential force from one side of the well to the other. This difference in force, even though very small compared to the total force of the JOG on the CL in the well, may then push the CL from the well. For another example, if the axis of the nozzle is shifted relative to the axis of the well even by a small distance, for example, by a distance that is 5% of the diameter of the well, the JOG may then cause a strong differential force on the CL from one side of the well to the other. Again, this difference in force, though small compared to the total force of the JOG on the CL in the well, may then push the CL from the well.

Therefore, to provide for a method and apparatus to allow a high-velocity in the JOG, but still not push the CL from the well, in the embodiments described here the well and nozzle are designed and aligned so as to make the forces relatively symmetric about the axis of the well so that large impaction forces on the VCL on one side of the axis tend to be canceled by similarly large impaction forces on the opposite side of the well.

In our preferred embodiments both the nozzle and the well have a circular cross section and the axis of the well and the axis of the nozzle are collinear. In this way the nozzle is positioned relative to the well so as to reduce the forces tending to push the CL out of the well, even when a high-velocity JOG is used to provide impaction forces sufficient to collect the small particles.

Preferably, the cross section of the nozzle is not small relative to the cross section of the well, because if the nozzle is small and positioned close to the well, the forces the JOG may cause large radially varying forces on the CL in the well. Although these axisymmetric forces are not as likely as the non-axisymmetric forces to push the CL from the well, if they are large enough then they cause enough instability in the CL so that it can be pushed from the well.

For most applications where significant effort is expended to obtain the gas sample that is drawn into the nozzle (e.g., in applications where the particles in the gas have already been concentrated in an air-to-air concentrator), then preferably the cross section of the well is approximately equal to the cross section of the JOG. So configured, the gas-liquid surface is sufficiently large relative to the cross section of the JOG at the position of the gas-liquid surface, so that the JOG does not tend to cause highly asymmetric forces on the VCL, but also so that the JOG is not so large that a large fraction of the particles in the JOG that would impact on a large flat surface, do not impact on the CL in the well.

For some other applications, for example where no preconcentration of the aerosol particles in the air is used and the electrical power required for the pump is not a problem, but the volume of the CL used is to be minimized, then the diameter of the JOG may be significantly larger, e.g., 60% larger, than the well. Then many particles in the JOG have no chance of impacting on the CL in the well, but the flow of the JOG near the CL in the well may be more uniform.

In some embodiments, the shape and size of the cross section of the nozzle and the cross section of the well are aligned and substantially similar, where "similar" has the meaning it does in geometry (same shape but not necessarily the same size). Such is the case in the embodiment of FIG. 3. In these embodiments the "average normal to the gas-liquid surface" is collinear with the axis of the well.

Nozzles used for impaction of particles onto a surface have been studied and used extensively (see for example W. C. Hinds, p. 121-134.).

Note that the nozzle 302 and the well 304 of the embodiment of FIG. 3 are aligned so that they share the same axis. Thus, if the nozzle were pushed in along the axis of symmetry, in the direction of the well until the nozzle came in contact with the well, the cross section of the nozzle would overlap with the cross section of the well.

In other embodiments, the cross section of the well and of the nozzle may be different sizes. In this regard, a potential advantage of having the cross section of the well slightly larger than that of the nozzle is that the collection efficiency for the particles may be higher. This is especially the case in which the distance between the nozzle and the gas-liquid surface of the VCL in the well is relatively large.

Although depicted in the embodiment of FIGS. 1, 2, and 3 as having an exposed surface of the CL positioned in a substantially horizontal orientation, and an axis that is collinear with a vertical line, capillary forces are typically strong enough to hold the CL in the small-diameter wells so that these wells need not face upward. This is because gravity can be a relatively small or negligible force in these small diameter wells.

In some embodiments, various techniques can be used for determining whether an appropriate amount of CL is contained in a well. By way of example, electrodes can be positioned near the desired level of the VCL held in the well. A resistance between these electrodes can then be measured, so that the height of the VCL in the well can be determined. Pressure adjustments in the collection liquid reservoir then could be used to maintain the height of the CL in the well somewhat constant.

As another example, a laser diode can be used to illuminate the VCL. A photodetector then can be located to measure the light scattered by the VCL so that this measurement of the scattered light can be used to determine if the size of the VCL is becoming smaller than desired. If so, a collection liquid pump can be directed to pump more collection liquid into the VCL.

In some embodiments, an aqueous CL is used. In other embodiments, the CL is a nonaqueous solution, which may be chosen in part because of its low evaporation rate.

In some embodiments, the well and CL in the well are cooled in order decrease the evaporation rate and also to increase the viscosity, which can enhance the stability of the CL in the well. For example, the vapor pressure of water at 0° C. is 0.61 kPa, while at 20° C. it is 2.33 kPa, and at 40° C. is 7.38 kPa. The evaporation rate decreases as the vapor pressure decreases. The viscosity of water at 0° C. is 1.79 millipascal seconds, while at 20 0° C. is only 1.0 millipascal seconds. In some embodiments in which the CL is cooled, the ALC can further include a temperature sensor to monitor the temperature of the CL in the well or at some point near the well.

In some embodiments, the ALC includes a means to cool the gas before it exits from the nozzle as a JOG so that the JOG has less of a tendency to warm the CL in the well. Thus, the rate of evaporation of CL in the well can be reduced. In some embodiments in which the gas is cooled, the ALC further includes a temperature sensor and a humidity sensor to monitor the temperature and humidity of the gas entering the inlet 126, so that the rate of cooling of the gas can be controlled so that no condensation occurs in the inlet 126 or nozzle.

In some embodiments, the CL contains solute molecules that reduce the vapor pressure (as described by Raoult's Law at the lower concentrations) and thereby reduce the evaporation rate. In some of these embodiments, the solute molecules also increase the viscosity and thereby increase the stability of the CL.

One or more features or functional aspects can enable an ALC to collect particles with a CL even when the JOG moves at a high rate, e.g., 10 m/s, 20 m/s or faster. For example, the JOG can be coaxial with the well and so the forces on the CL in the well are symmetric about the axis of the well to a first order. Thus, asymmetric forces that can readily push the CL out of the well are reduced.

Additionally, or alternatively, in those embodiments in which the surface on the inside of the well is made from a material that has a low interfacial tension with the CL, and the surface immediately outside the well is made of a material that has a high interfacial tension with the CL (e.g., a hydrophobic surface with an aqueous CL), the non-symmetric perturbations of the type that would allow CL to be pushed from the well result in an increase in total interfacial tension. Therefore, such perturbations are not energetically favored.

Additionally or alternatively, in embodiments where the CL is cooled, the increase in viscosity of the CL contributes to the stability of the CL in the well. Notably, the viscosity of water at 0° C. is 1.79 millipascal seconds, while at 20° C. is only 1.0 millipascal seconds. One millipascal second is equivalent to one centipoise.

In some embodiments, the CL has a viscosity of less than approximately 8 millipascal seconds. For example, in some embodiments, the viscosity can be less than approximately 2 millipascal seconds.

Additionally or alternatively, the relative importance of surface tension increases as the volume of the collection liquid in the well decreases, in a manner similar to how surface tension tends to hold a small droplet more nearly spherical than it does a large droplet. In the VCL in the well, both the surface tension and interfacial tension can resist the changes in shape that are necessary for the VCL to leave the well.

Referring again to FIG. 3, this embodiment of an ALC incorporates a collection-liquid reservoir (CLR). The CLR stores CL so that an associated well (304) can be fed as needed with CL. The well 304 also connects to a tube 306 that bends to move CL toward an analyzer. That tube need not bend as illustrated, and for some applications where there is concern that the particles may settle in the CL and fall to the bottom of a tube that is bent horizontally, then the well may be connected to a tube that is straight or tapered-and-not-bent (see FIG. 4), and the tube is given an orientation with respect to the vertical such that the particles do not fall so fast that they land on the tube.

The collection of particles into the VCL is accomplished as follows with respect to the embodiment of FIG. 3. A collection-liquid pump (CLP) 312 that is connected to the CLR 310 pumps the CL into a collection-liquid tube (CLT) 314. The CL moves into the well that holds a VCL so that the CL can be exposed to a JOG exiting from the nozzle 302. Notably, the CLP may pump the CL into the CLT either continuously or at selected intervals.

Figure 3:
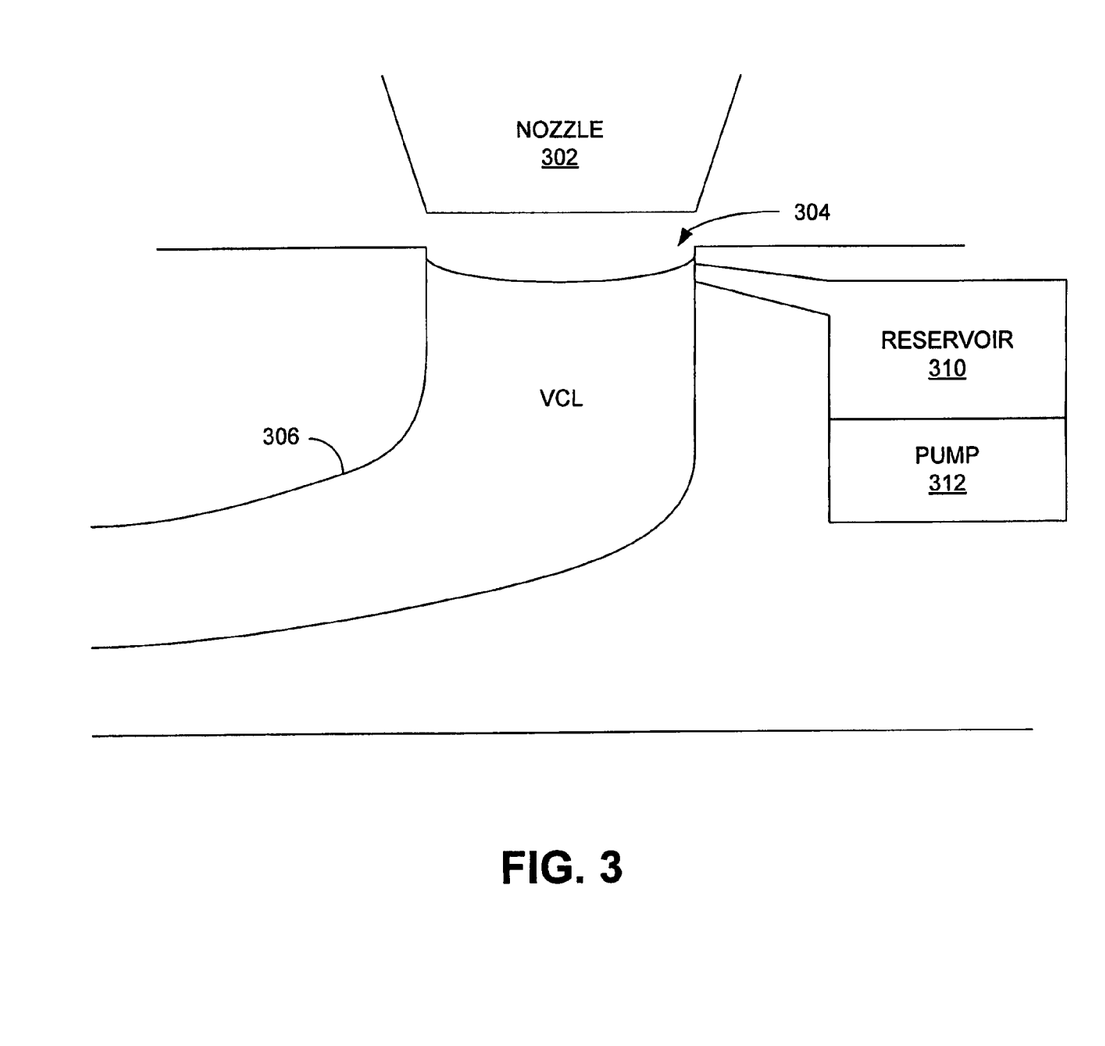
FIG. 3 is a schematic illustration of a side view of another embodiment of a system for collecting particles in which the collection liquid from a reservoir enters the well from near the top of the well, near the air-liquid interface.
Figure 4:
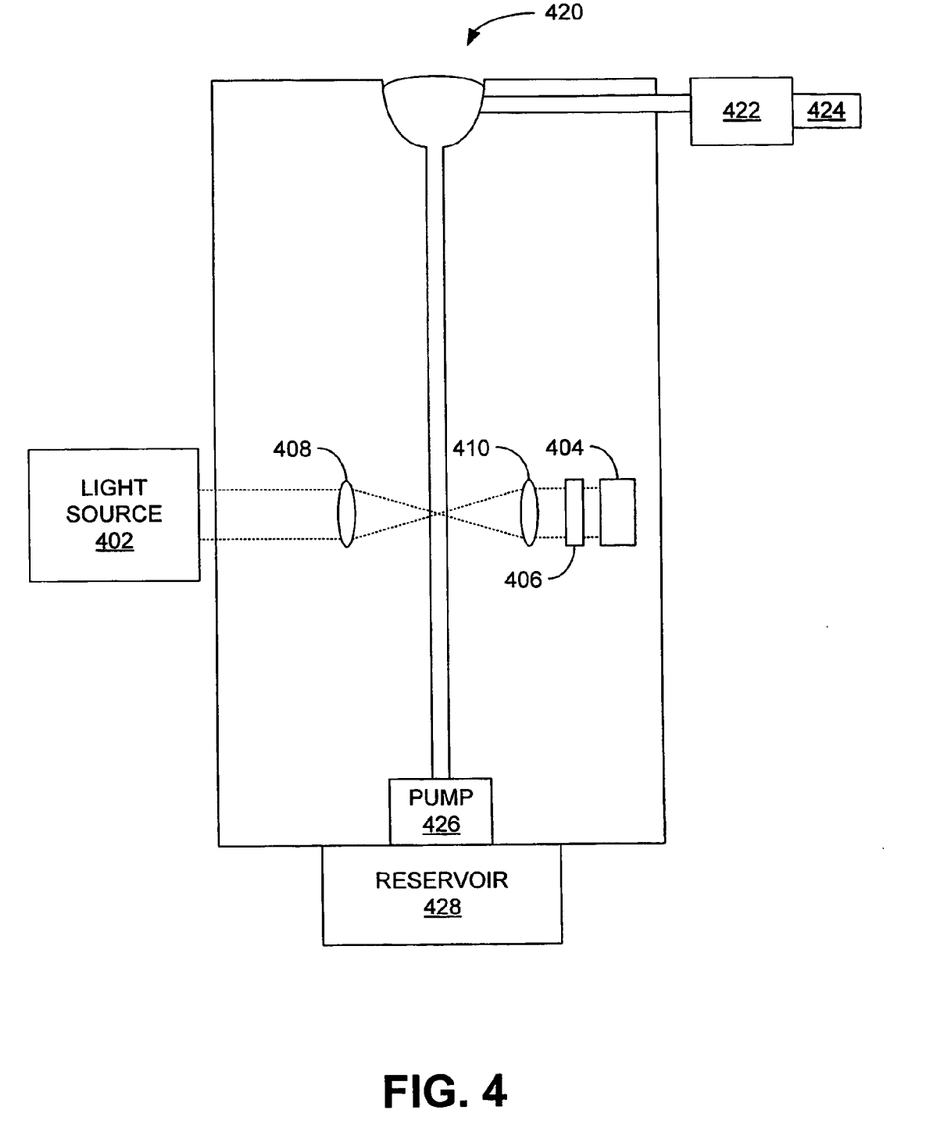
FIG. 4 is a schematic illustration of a side view of an embodiment of a system for collecting particles, showing an analysis system.

An embodiment, such as depicted in FIG. 3, can be operated in manner so that: (a) the well is filled with the VCL, (b) this VCL is exposed to the JOG exiting from the nozzle and becomes an EVCL, and (c) the EVCL is drawn out of the well for further analysis. In some embodiments, the EVCL is drawn from the well directly into an instrument that analyzes the collected particles for antigens, or their content of specific RNA's, or other materials. In some embodiments, an effluent pump, such as depicted in FIG. 4, helps control the rate that the CL flows out of the well. In some embodiments, this effluent pump is also part of whatever instrument analyzes the EVCL.

In some embodiments, the CL contains chemicals (used in the broad sense to include inorganic, organic, biochemical materials) that react with selected particles or all of the particles in such a way that the particles can be characterized using optical analysis. For example, in one embodiment, fluorescent-tagged antibodies (F-Ab) bind to specific antigens on particles of interest. The F-Ab make the particles of interest fluorescent and the tagged particles are detected optically, for example, by counting them with a microscope or a flow cytometer (see, for example, Howard Shapiro, Practical Flow Cytometry, $4^{th}$ ed., (Wiley, 2003), herein incorporated by reference, and C. Sakamoto, N Yamaguchi, and M Nasu, Rapid and Simple Quantification of Bacterial Cells by Using a Microfluidic Device, *Applied and Environmental Microbiology*. 71(2), 1117 (2005), herein incorporated by reference).

In some embodiments, an array of wells can be included, each of which may be in one CLC. In other embodiments, an array of CLCs can be included. In some of these embodiments, there can be fewer nozzles than there are wells. In some embodiments, there is only one nozzle. For the embodiments with fewer nozzles than wells, provisions can be provided for moving the wells and the nozzles relative to each other.

In some embodiments, there is a means to illuminate and count the particles in the wells. For example, if the particles of interest have specific antigens on their surfaces, and the CL includes F-Ab which specifically bind to these POI then the means to illuminate and count the particles can include a subsystem such as shown in FIG. 4. In particular, the subsystem includes a light source 402 to excite the fluorescence of the F-Ab, and a detector 404 that is sensitive to the fluorescence of the F-Ab. A filter 406 can be used to block from the detector any light that is from the light source but not from the F-Ab. Lenses, such as lenses 408 and 410, also are provided to focus the light from the source. In some embodiments, the optics are basically those of a fluorescence microscope, or of a fluorescence-based flow cytometer.

In embodiments that include F-Ab selected to bind to the POI, then these F-Ab bind to the POI, and as these F-Ab-tagged particles move down through the vertical tube they are counted at some point that is far enough down the tube that the F-Ab have had sufficient time to bind to the POI. Notably, although the collection of particles that are biological has been emphasized here, the application of this invention is not restricted to collection of particles that are biological, nor is it restricted to atmospheric particles, but it may apply to, for example, particles in the air in a hospital, or in a clean room, or in an agricultural facility, or in any number of other places where it is important to characterize gas-borne particles.

In operation, the embodiment of FIG. 4 provides CL to a well 420 from a CL reservoir 422 using a pump 424. The CL then collects particles such as described before. An effluent pump 426 draws the CL from the well and directs the CL toward the analyzer for optical analysis. Once analyzed, the CL can be collected in a reservoir 428.

It should be noted that, in some embodiments, a valve can be located between the reservoir and the well in order to prevent CL from flowing back into the reservoir. Additionally or alternatively, a valve can be located between the well and a downstream analyzer. So located, such a valve could prevent ice, for example, from entering the analyzer. Preferably, at least this valve is of such a type that does not tend to collect particles, i.e., particles in the CL do not tend to adhere to the valve.

In embodiments that incorporate multiple wells per analyzer subsystem, there is also a means to provide the CL with the particles contained therein from each well to the analyzer. For instance, in some embodiments, the wells can be repositioned relative to the light source and detectors so that the POI can be analyzed in turn. In some embodiments, plumbing can be provided so that all of the arrayed components can share the same pump(s). In some of these embodiments, the pressure difference can be applied sequentially from one ALC to the next, with whatever timing is required.

Several experimental examples will now be described in detail.

In a first example, holes (to make wells) of various diameters were drilled to a shallow depth (e.g., 1 mm) into a piece of clear plastic. Water was placed in these wells using a needle and syringe. 1 L/min of air was then blown through a 1 mm nozzle that was positioned directly above the hole, where the air exiting the nozzle was aimed directly at the hole. Notably, the nozzle was not designed for this purpose, but was a glass pipette. The tip of the nozzle was not very smooth, which was a concern because the flow exiting cannot be as uniform as if it were completely symmetric, and for cases that are on a borderline between blowing-the-liquid-out-of-the-hole and having-the-water-stay-in-the-hole, lack of symmetry can be relevant.

With 1 L/min exiting through the 1 mm diameter nozzle (the glass pipette) the following aspected were noted. First, with about 20 mL of water in a beaker, the air blew a hole down into the water that could be over 1 cm deep. Second, with a water puddle on a metal surface, the air blew a hole through the puddle directly down to the metal surface (approximately 2 mm deep). Third, with a 1.6-mm-diameter well, the liquid could be blown out of the hole. This is a case where probably if the nozzle has a more symmetric tip, and if there were minimal turbulence in the air in the room (and better yet, if the nozzle and well were in a container as in the figures), and if the nozzle were positioned in an ideal way (perfectly vertical and centered), and if the material outside the region where the water was to be in contact were hydrophobic, then it is very likely that the water could be kept in the hole with 1 L/min blowing on the water.

Fourth, with holes that had diameters of 1 mm (and 2 mm deep), 0.66 mm (1.32 mm deep), and 0.41 mm (0.81 mm deep), then the 1 L/min air flow did not blow the liquid out of these holes. Note that for the two smaller diameters mentioned above, the nozzle is significantly larger than the well diameter, and so the analysis presented above for calculating $d_{50}$ don't apply directly. These holes were drilled with a Vectra milling machine, which allows a good approximation of the depth. The nozzle was significantly less than 1 mm away at its closest from the surface of the well. It seems that this particular system could work quite well with the water surface, for example, 0.3 mm below the surface of the plastic.

It was observed that the 1 L/min does not blow the liquid out of the holes that are as large as 1-mm-diameter. Additionally, even better collection efficiencies for the smallest particles can be obtained with smaller nozzle-to-surface distances as described above with reference to the article by Grinshpun et al., incorporated by reference. These observations, along with the descriptions of collection efficiencies described above and in Hinds, incorporated by reference above, combine to suggest strongly that it should be possible to obtain reasonably good collection efficiency into a 1-mm-diameter water surface for particles throughout the total 1 to 10 um diameter range. In this regard, "reasonably efficient" means 20% or greater. Notably, this most likely underestimates the collection efficiency for 1 um diameter particles, and grossly underestimates the collection efficiencies for particles 1.5 or 2 um diameter or larger.

Although, in the first example of the collection tube with hole into it from the side the tube is 1 mm diameter, use for BW aerosol detection could use tubes with smaller diameters. The specific diameters used may depend upon a variety of other design parameters. For building a system for a particular application, the diameters and flow rates may be different. For example, if an air-to-air concentrator with a 0.25 L/min output is used, then a nozzle with approximately half the diameter of 1-mm-diameter nozzle could give the same exit velocity. Then, either the collection liquid could be kept in the 1-mm-diameter hole, in which case the collection efficiency may be higher than in the case of the 1-mm-diameter nozzle 150, or the diameter of the hole that holds the collection liquid could be smaller, and the volume of the collection liquid may be smaller.

In a second example set of experiments, plastic disposable micropipette nozzles were used for both the nozzle and the well. The nozzle used for the well was connected to a syringe that was filled with water (the CL), so that the CL could be replenished if it evaporated or if any bubbles in the liquid were compressed. This also enabled the effects of the JOG on the CL to be studied as the level of the CL in the well varied, and as the CL protruded from the well. The perceived advantages of these micropipette nozzles are: 1) the plastic comprising these micropipette nozzles is more hydrophobic than either the plastic that we used in the first example, which seemed to become less hydrophobic with time, or the glass of the glass pipettes that were used in some experiments; 2) the walls of these nozzles, especially near the tip is are relatively thin, and are thin enough that it is relatively easy to see the surface of the liquid and, 3) These nozzles can be easily connected to a syringe filled with water so that they can be filled easily and the position of the liquid in the well most easily controlled.

In this second example, the nozzle diameter and well diameter is about 0.5 mm. The highest air flows that we impacted on the liquid at the opening of the well were between about 0.4 L/min and 0.45 L/min. Assuming a nozzle to liquid surface spacing of 0.5 mm, which is a good assumption, and assuming unit density spheres (1000 kg/m$^3$), then using Hinds, Eq. 5.29, the calculated $d_{50}$ is 0.68 micrometer. As discussed above with respect to the Sethi and John paper incorporated by reference, the collection efficiency into a 0.5 mm well using a 0.5-mm-diameter nozzle exit will result in some of the particles that would be collected onto a solid surface not being collected into the well. We do note that the diameter of the CL just outside the well could form a somewhat spherical surface with a diameter a little larger than the well.

In this second example, the CL could be pushed from the well with the syringe when the velocity of the JOG was very low, so that the CL formed a shape something like a half sphere. Then when the velocity of the JOG was increased it could change the shape of the half-sphere meniscus into a flattened half-sphere where there appeared to be a dip into this half-sphere at some velocities. The hydrophobic surface of the nozzle reduced the tendency for the CL to leave the nozzle.

For typical application to detection of aerosolized BW agents, an air-to air concentrator is likely to be used. Such concentrators have been used in combination with a variety of aerosol detectors and collectors to concentrate the particles in air before they enter the detector or collector. Examples of commercially available virtual-impactor concentrators are the MicroVIC sold by Mesosystems, from Albuquerque, N. Mex., and the XMX sold by Dycor Technologies, Ltd., Edmonton, Canada. For some applications, it may be useful to employ such an aerosol concentrator in combination with the ALC, so that more particles can be collected from gas for a given concentration of particles in the gas.

In some embodiments, the ALC includes a system for sorting aerosols, such as described in US patent application, US 2005/0028577 A1, Feb. 10, 2005, by Richard Kounai Chang, Jean-Pierre Wolf, Veronique Boutou, and Yong-Le Pan, "Systems and Methods for Sorting Aerosols," herein incorporated by reference. In these embodiments, this system for sorting aerosols is connected to the gas inlet. For particles about 2-um diameter and larger it is possible to reduce reagent using such a system to select particles that have some characteristic feature of the particles that need to be analyzed, e.g., they contain the laser-induced fluorescence (LIF) spectrum similar to tryptophan. A limitation of this approach is that it may have a very low sensitivity if particles that have low mass-mean diameter (e.g., 1 micrometer). Therefore, in some embodiments the ALC includes two ALC. A means to split the incoming flow of gas so that some of the gas is run directly to one ACL is provided and some of the gas is run through a system for sorting aerosols before going to its ACL. By splitting the input air between the two systems, higher sensitivity for large mass-mean-diameter particles, but still measuring with a good sensitivity the very small mass-mean-diameter particles is potentially achieved.

In some embodiments, the ALC includes an air-to-air concentrator for concentrating particles from a larger volume of air into a small volume of air. Such a concentrator could be connected to the gas inlet. The virtual impactor concentrator is one example of an air-to-air concentrator that is used in some embodiments. The XM-2 as purchased from Dycor is an example of such a virtual-impactor concentrator.

Figure 5:
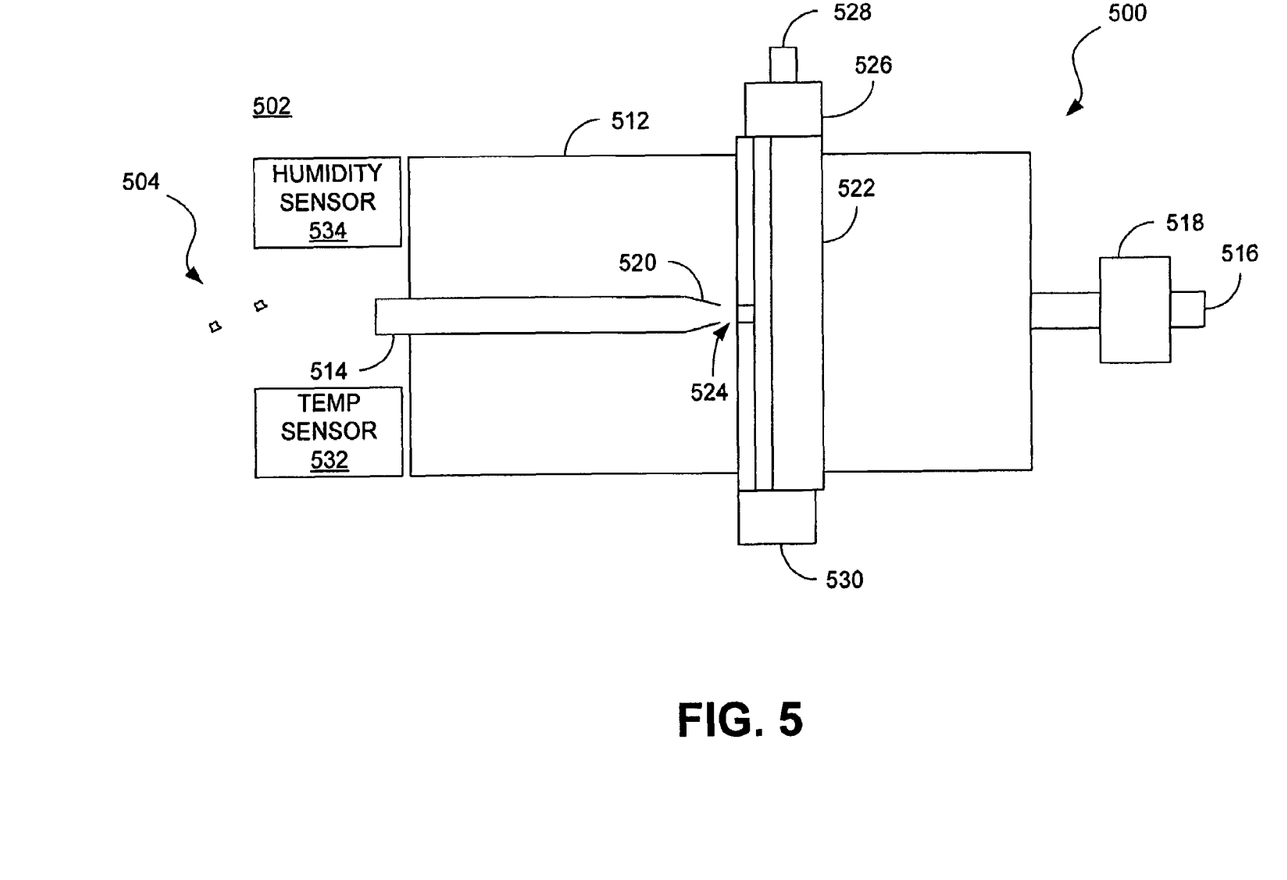
FIG. 5 is a schematic illustration of a side view of another embodiment of a system for collecting particles.

FIG. 5 is a schematic diagram illustrating another embodiment of a system for collecting particles. In particular, the system incorporates an aerosol-into-liquid collector (ALC) 500. The ALC 500 is immersed in a gas 502 having particles 504 therein. The ALC 500 incorporates a container 512, such as a gas-tight container (GTC), a gas inlet 514, a gas outlet 516 and a source of vacuum pressure 518. The gas inlet pneumatically communicates with a nozzle 520.

The source of vacuum pressure 518 is configured such that, when the source of vacuum pressure generates a vacuum, a gas is drawn into the container through the gas inlet with as high a velocity as is desired.

A collection-liquid container (CLC) 522 also is provided that includes a well 524. The well holds a volume of the collection liquid (VCL). The well is positioned so that particles entrained in gas entering the container 512 collide with the VCL and may adhere to the VCL.

Notably, the well 524 that holds the VCL is positioned sufficiently close to the nozzle so the velocity of the JOG near the gas-liquid surface is sufficiently large so that a substantial fraction of the particles within the preselected range of sizes are caused to impact into the VCL at the gas-liquid surface. Additionally, the well is positioned relative to the nozzle such that the JOG impinges upon the gas-liquid surface in such a manner that any forces on the VCL arising from the JOG are relatively symmetric about an average normal to the gas-liquid surface. This is done so that the JOG does not tend to push the VCL out of the well.

The embodiment of FIG. 5 also includes a CL reservoir 526 from which CL is provided by a pump 528. An effluent pump 530 is configured to draw the CL from the well and to direct the CL toward an analyzer (not shown) for analysis. Additionally, a temperature sensor 532 is provided that measures a temperature of the gas at the inlet 126 to the container 512. Additionally, for embodiments in which the collection liquid is aqueous, a humidity sensor 534 is provided that measures the humidity of the gas at the inlet 126 to the container. Additionally, in some embodiments an aerosol particle counter, which may be a simple light scattering particle counter similar to those sold by Particle Measurement Systems or an aerodynamic particle sizer as sold by TSI Inc., is connected to the ALC in order to measure the numbers of particles in different sizes in the gas outside the ALC. In this regard, the temperature, humidity, and particle numbers measured by the temperature sensor, the humidity sensor, and the aerosol particle counter respectively, are used, at least in part, to determine rates and times at which the CL is moved with respect to the well, e.g., when more CL is to be added. For example, the aerosol concentration in the gas can be used to help estimate when the particle load collected into the well is approaching a level that is likely to be larger than is best for the analytical technique, and so the CL should be moved out and replaced.

Additionally, a liquid level sensor (not shown) can be incorporated near the rim of the well. In some embodiments, such a sensor can be as simple as two electrodes, one on each side of the well, and the conductivity between these two electrodes is measured, and used to determine if the liquid level has dropped.

Additionally or alternatively, a means to reduce or stabilize the temperature of the CL in the well in order to reduce the evaporation of the CL can be provided. In such a case, it is useful to have a temperature sensor in the CLC near or even inside the well so that a feedback loop can be used to maintain the temperature of the CL at some desired set point, and also to not freeze the CL in the well.

Figure 6:
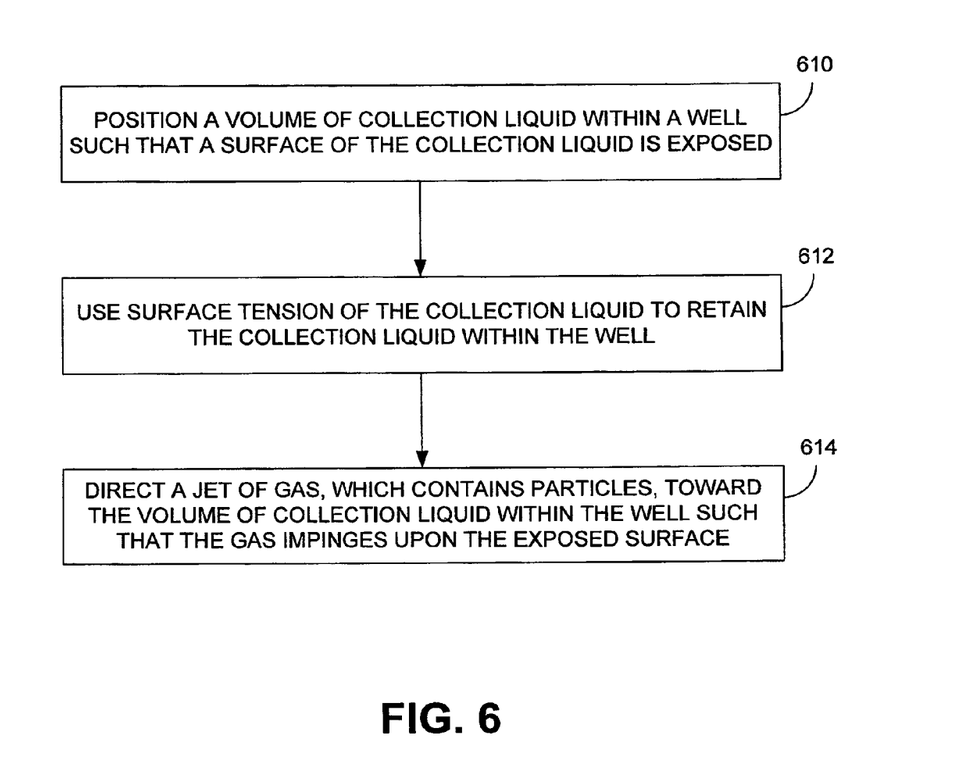
FIG. 6 is a flowchart illustrating functionality of an embodiment of a system for collecting particles.

In this regard, FIG. 6 is a flowchart illustrating functionality, such as the functionality exhibited by the embodiment of FIG. 5. As shown in FIG. 6, the functionality (or method) may be construed as beginning at block 610, in which a volume of collection liquid is positioned within a well such that a surface of the collection liquid is exposed. In block 612, surface tension of the collection liquid is used to retain the collection liquid within the well. In block, 614, a jet of gas, which contains particles, is directed toward the volume of collection liquid within the well such that the gas impinges upon the exposed surface of the collection liquid.

It should be emphasized that many variations and modifications may be made to the above-described embodiments. All such modifications and variations are intended to be included herein within the scope of this disclosure and protected by the following claims.

I claim:

1. A system for collecting particles comprising:
   an aerosol-into-liquid collector operative to position a collection liquid to capture particles entrained in a gas, the aerosol-into-liquid collector comprising:
   a nozzle operative to direct the gas with the particles entrained therein at a velocity of at least 10 meters per second; and
   a well operative to hold a volume of the collection liquid and being positioned such that at least some of the particles entrained in the gas collide with an exposed surface of the volume of the collection liquid and adhere to the volume of the collection liquid;
   wherein the gas, with the velocity of at least 10 meters per second, departing said nozzle and impinging upon the exposed surface of the volume of the collection liquid does not push the volume of the collection liquid out of the well and does not cause the volume of the collection liquid to break into multiple droplets, and
   said nozzle has an interior nozzle diameter and the exposed surface of the collection liquid is positioned at a distance less than two times the interior nozzle diameter from the nozzle; further,
   the interior nozzle diameter and the diameter of said well are each less than about 1.4 millimeters.

2. The system of claim 1, wherein the aerosol-into-liquid collector further comprises a container, a gas inlet, a gas outlet and a source of vacuum pressure such that, when the source of vacuum pressure provides vacuum pressure at the gas outlet, gas with particles entrained therein is drawn into the container through the gas inlet and is provided to said nozzle.

3. The system of claim 1, wherein the volume of the collection liquid into which the particles are collected is no greater than approximately 4 microliters.

4. The system of claim 1, wherein:
   spacing between the exposed surface of the volume of collection liquid and the nozzle is no greater than approximately 1 millimeter.

5. A method for collecting particles comprising:
   positioning a volume of a collection liquid within a well such that a surface of the collection liquid is exposed;
   using surface tension of the exposed surface of the volume of the collection liquid and the interfacial tension between the collection liquid and the well to retain the collection liquid within the well, with an effect of the surface tension of the exposed surface of the volume of the collection liquid and the interfacial tension between the collection liquid and the well exceeding an effect of gravity in maintaining the collection liquid within the well; and
   directing a jet of gas, which contains particles, toward the volume of the collection liquid in the well such that the gas impinges upon the exposed surface;
   wherein a velocity of the jet of gas impinging upon the exposed surface of the volume of the collection liquid permits particles of less than 2 micrometers in diameter to be collected into the collection liquid while the surface tension of the exposed surface of the volume of the collection liquid and the interfacial tension between the collection liquid and the well prevent the collection liquid in the well from breaking into multiple droplets and from being pushed from the well.

6. The method of claim 5, wherein the well is circular with a diameter no greater than 1.3 micrometers.

7. The method of claim 5, wherein the well is circular with a diameter no greater than 0.8 micrometers.

8. The method of claim 5, further comprising cooling the collection liquid in the well.

9. The method of claim 5, further comprising cooling the jet of gas before the jet of gas impacts the exposed surface such that a tendency of the jet of gas to warm the collection liquid in the well is reduced.

10. The method of claim 5, further comprising analyzing particles contained in the collection liquid.

* * * * *